United States Patent
Shanbrom

(12)
(10) Patent No.: US 6,361,786 B1
(45) Date of Patent: *Mar. 26, 2002

(54) MICROBICIDE TREATED POLYMERIC MATERIALS

(75) Inventor: Edward Shanbrom, Santa Ana, CA (US)

(73) Assignee: Shanbrom Technologies, Ojai, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/619,888

(22) Filed: Jul. 20, 2000

Related U.S. Application Data

(63) Continuation-in-part of application No. 09/158,939, filed on Sep. 22, 1998, now Pat. No. 6,183,764, which is a continuation-in-part of application No. 08/929,415, filed on Sep. 15, 1997, now Pat. No. 5,811,471.

(51) Int. Cl.$^7$ .......................... A01N 25/00; A61M 31/00
(52) U.S. Cl. .................. 424/405; 424/484; 424/486; 522/75; 604/508; 604/512; 604/513
(58) Field of Search ............... 523/122; 424/405, 424/484, 486; 604/508, 512, 513; 522/75

(56) References Cited

U.S. PATENT DOCUMENTS

| | | | | |
|---|---|---|---|---|
| 4,087,597 A | * | 5/1978 | Hafeli | 526/5 |
| 4,584,188 A | * | 4/1986 | Graham | 523/122 |
| 4,999,386 A | * | 3/1991 | Oakes | 523/122 |

* cited by examiner

*Primary Examiner*—Morton Foelak
(74) *Attorney, Agent, or Firm*—Stefan J. Kirchanski, Esq.; Crosby, Heafey, Roach & May LLP

(57) ABSTRACT

A microbicidal organic polymer material for use in manufacturing of contact lenses, catheters, condoms, surgical sutures and gloves, medical examination devices and similar uses is provided by polymers to which is tightly adsorbed a disinfectant organic dye. Many polymers such as polyvinyl chloride and acrylic polymers show exceptional avidity for a number of microbicides, of acidic, basic, aromatic and/or hydrophobic character such as methylene blue and gentian violet. Consequently, devices constructed of these polymeric materials release no free dye to an aqueous solution. The material is generally a natural or synthetic polymer that releases no particles or fines into wounds or body orifices. Presence of adsorbed disinfectant organic dye allows the polymer to inhibit microbial growth in a number of different situations. Several common microbes are killed by being incubated in the present of an embodiment of the invention that contains a combination of methylene blue and gentian violet. Absorption of meglumine to the polymers in combination with the organic dyes enhances the anti-infective properties of the material.

10 Claims, No Drawings

MICROBICIDE TREATED POLYMERIC MATERIALS

The instant application is a continuation-in-part of application Ser. No. 09/158,939, filed Sep. 22, 1998, now U.S. Pat. No. 6,183,764, which was a continuation-in-part of Ser. No. 08/929,415, filed Sep. 15, 1997, now issued as U.S. Pat. No. 5,811,471.

BACKGROUND OF THE INVENTION

1. Field of the Invention

The present invention is related to the medical products and personal care products and especially to natural and synthetic polymers used to manufacture contact lenses, polymeric medical sutures, surgical gloves, and other similar medical items.

2. Description of Related Art

The importance of sterile techniques to modem medicine can hardly be overestimated. Almost every medical student is aware of infections introduced during surgery or during post surgical care and all users of contact lenses are familiar with the importance of clean contact lenses to the health of their eyes. A continuing problem with the use of polymeric materials has been the propensity for microorganisms to adhere to surfaces of these initially sterile polymeric materials which bacteria can subsequently lead to irritation and/or infection. The principal uses of medical grade polymers puts them in contact with various mucosal and other surfaces of the human and mammalian body. These surfaces are key to the body's early line of defense. When mucosal surfaces are abraded, penetrated or exposed to conditions conducive to microbial growth, infection can more readily occur. To inhibit infection, polymeric materials coming in contact with mucosal surfaces could be treated with a microbicide to inhibit microbial adhesion and subsequent microbial growth leading ultimately to infection. Unfortunately, it has proven difficult to provide an effective microbicide that does not readily wash out of the material, thereby greatly reducing its effectiveness and possibly causing irritation or damage to body tissues.

In most cases polymeric products are sterilized by treatment with gases or radiation prior to packaging; however, once in contact with mucosal or other tissue surfaces they act as a substrate for adherence and multiplication of microbes. Various microbicides have been investigated, but in most cases they are released from the polymer under aqueous conditions and are then more or less toxic to body tissues. What is needed is an agent that kills or inhibits microbial growth and adherence which remains adsorbed to the polymeric material under various physiological conditions where it can function without having negative effects on living tissue.

OBJECTS AND SUMMARY OF THE INVENTION

Therefore, it is an object of the present invention to provide adsorbent materials with anti-microbial properties for use in devices which ideally can remain in contact with mammalian mucosal surfaces or tissues for short to medium term duration without introducing or supporting microbial growth.

It is a further object of the current invention that the materials with antimicrobial properties not irritate surrounding tissues.

These and additional objects that will become apparent to one of ordinary skill in the art upon reading the following specification are provided through the use of polymers treated with crystal (gentian) violet and/or the microbicidal components from various fruits such as species of Vaccinium, (i.e., blueberry, bilberry, cranberry, and lingonberry) as well as aronia berry (Amelanchier), species of Rubus (raspberry and blackberry) and species of Vitis (grape). Various organic polymers demonstrate sufficient avidity to remove a number of microbicides from physiological solutions, including those mentioned above. Consequently, devices constructed of these materials, which have been treated with microbicide(s), release insignificant quantities of microbicide into aqueous solution. The presence of adsorbed microbicide(s) allows the polymer to inhibit microbial growth in a number of different situations. This makes the invention ideal for any uses where microbe-free adsorbent material is needed.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a method of treating the polymer with an adsorbed microbicide from a concentrated solution of crystal (gentian) violet or other microbicidal/disinfectant dye in order to provide polymeric surfaces which resist microbial growth and adhesion significantly more than their untreated equivalent.

By "microbicide" of "disinfectant" is meant any of a number of organic dyes, generally known as "vital dyes," including methylene blue and related thionine dyes (electronegative or acidic), acridine orange, acridine yellow and related acriflavine (acridine) dyes (electropositive or basic), quinacrine and its derivatives, brilliant green, crystal violet (gentian violet, C.I. Basic Violet 3), and related triphenyl methane dyes (electropositive), and bis naphthalene microbicides such as trypan blue and trypan. Methylene blue and crystal (gentian) violet are especially preferred, but the invention is not limited to these synthetic dyes. Various plant fractions—generally polyphenolic pigmented compounds such as anthocyanins from fruits—are also effective when adsorbed onto polymeric surfaces.

The cause of the microbicidal property of the dyes and appropriate plant fractions is not entirely known. Since many of the dyes have oxidation-reduction (redox) potentials in the range of many electron transport components of oxidative metabolism, it seems possible that such dyes may operate by "short circuiting" electron transport pathways. Also, the dyes may operate by interacting with genetic material (nucleic acids). Generally, the synthetic dyes show differential activity towards Gram-negative versus Gram-positive bacteria with electronegative (acidic) dyes being more effective on Gram-negative bacteria and electropositive (basic) dyes being more effective on Gram-positive bacteria such as *Staphylococcus aureus*. This might suggest that these dyes operate by binding to the membranes or cell walls of the bacteria. The various fruit factors are generally polyphenolic materials with antioxidant properties. It is known that such phenolics can show antimicrobial activity although the precise reason for this activity is still open to conjecture.

In the original parent of the present application the inventor discovered that synthetic disinfectant dyes bind strongly to polyvinyl acetal (PVA) forming a germicidal or bacteria resistant material. In the course of those studies the present inventor discovered that a variety of plastic polymers such as polyvinyl chloride may also binds the disinfectant dyes although, in some cases, not as effectively as PVA. Nevertheless, polymers treated with disinfectant dyes become highly resistant to bacterial growth—even causing a "zone of inhibition" when placed on a bacterial culture plate. The useable polymers include at least polyvinyl chloride, latex, polyurethanes, polyacrylates, polyester (i.e., polyethylene terephthlate) polymethacrylates, silicone rubber (and related silicon elastomers) polystyrene, polycarbonates and polysulfones. The polymers, polyvinylchloride and hydroxymethylmethacrylate, used to demonstrate the present invention are medical grades that are already widely used in commercial manufacturing of surgical tubing and contact lenses, respectively. The relevant properties of these polymers are their ability to preferentially adsorb various microbicides or disinfectant dyes. When treated with the appropriate dye the polymers become more or less distinctly colored by the dye. However, in many applications, a colored polymer is not a drawback; especially when the color is an indication that the polymer is capable of resisting bacterial growth.

The antimicrobial material of the present invention is produced by adsorbing an effective quantity of one or more synthetic dyes or natural polyphenolic plant fractions to an appropriate polymeric material. An "appropriate" polymeric material means a polymer with sufficient avidity for a particular dye or factor in order to inhibit microbial adherence and/or growth under a variety of physiological conditions. For example, an acrylic plastic is used in "hard" contact lenses. When these lenses are pretreated with gentian violet or methylene blue, they are much less likely to provide a surface for microbial adherence and/or growth. This makes them less likely to lead to microbial infection of the eye. This can prolong the total useful life of the lenses and/or their time of use between cleaning procedures. Properties required for a given application are well known to those of skill in the art. Polymers that can be readily dyed with disinfectant dyes are already used in a variety of personal and medical care products e.g., polymeric contact lenses, condoms, catheters, etc. The same grade of polymers can be used for those applications with the current invention. "Effective quantity" means enough dye or plant fraction (pigment or polyphenolic fraction) to inhibit microbial growth over the projected period of use.

Generally, it is sufficient to soak the polymeric material in an excess volume of an aqueous solution of an appropriate disinfectant dye or plant fraction followed by thorough washing in solutions mimicking physiological conditions of use to remove non-absorbed or loosely-absorbed material. In many cases the process can be accelerated by including an organic solvent such as ethanol and/or ethoxyethanol. Of course, solvents that do not damage or dissolve the polymer must be used. This process can be readily automated by checking the wash water spectrophotometrically to ensure complete removal of non-absorbed antimicrobial material. Initial experiments have applied the antimicrobial material in aqueous solution. Many of the organic dyes are more soluble in ethanol than in water, this solvent can be used in cases where the polymer itself is not soluble in ethanol. Many dyes and plant fractions are quite soluble in glycerin, propylene glycol, ethylene glycol monomethyl ether or other "ethoxylated" or "methoxylated" alcohols. Ethers of the "glyme" series are also effective. Treatment solutions containing 50% or more of one of these solvent may be very useful depending on the polymer to be treated. Other appropriate solvents are known to those of ordinary skill or can be readily determined by examining available tables of dye solvents and comparing these to the known solvent resistance of the various polymers. Some of the polyphenolic plant fractions may be more difficult to dissolve; however, many are soluble in acidified methanol. The present inventor has found that soluble polyvinylpyrollidone (PVP) can be used to bring many plant polyphenols into solution.

In one test a 2×2 inch squares (one quarter inch thick) of polyvinyl chloride were covered with a 4 mg/ml aqueous solution of gentian violet (C.I. Basic Violet 3), and non-absorbed dye washed away with distilled water after a 30 min binding period. The treated polymer was then exposed to a 2.0 ml of a suspension of either *Escherichia coli* or *Staphylococcus epidermidis*. After a 30 min incubation, the squares were rinsed with physiological saline and introduce into bacterial nutrient broth. After 24 hr incubation at 37° C. the tube were read spectrophotometrically. While the *E. coli* showed a reading of 0.5 absorbance units the reading in the *S. epidermidis* samples was only slightly above background. Controls run with non-treated polymer showed readings of 1.2 and 0.8 absorbance units, respectively. This demonstrates the known result that basic dyes are more effective on Gram positive (Staphylococcus) than on Gram negative (Escherichia) microbe. The significant point here is that while a goal of the present invention is to suppress microbial growth, this experiment also demonstrates actual microbial killing.

A more realistic test of the present invention treated the 2×2 test squares with a mixture of both a basic (gentian violet) and an acidic (methylene blue) dye. The squares were treated with an aqueous stock solution containing 4 mg/ml of each of the two dyes. After washing, the squares were treated with 1.0 ml of microbial growth medium containing either 100 cells of *E. coli* or *S. epidermidis*. The squares were incubated for 24 hr at 37° C. and then read. As would be expected from the earlier experiment, all of the *S. epidermidis* cells were killed and no colonies grew up. Significantly, there were no colonies from the *E. coli* treatments either. Control material without the dyes showed abundant microbial growth. Significantly the dye mixture killed both Gram positive and Gram negative microbe. The experiment was repeated with *Yersinia enterocolitica* (Gram negative), *Serratia marcesceus* (Gram negative) and *Staphylococcus aureus* (Gram positive), and again there were no viable microbes following the treatment. Thus, a mixture of basic and acidic dyes adsorbed to polyvinyl chloride prevents the growth of a wide variety of common microbes. Repeating this experiment using blood or plasma as the microbial growth medium gave similar results indicating that an important goal of this invention, i.e., microbicidal activity in the presence of protein solutions, has been met. These experiments show that this material is ideal for medical or surgical grade materials, or polymeric contact lenses.

The experiments were repeated using acrylic plastics and urethane plastics. The subject plastics were soaked in the dye solution for a sufficient period to become lightly colored. The bacterial results were substantially the same as with polyvinyl chloride. From this it would appear that the exact polymer used is not critical as long as it is capable of binding a visible amount of dye. Thus, the treatment period should be adjusted, depending on the polymer, to yield visible color.

GLOVES

Ordinary latex examination gloves were stained by immersion for 6 hr in an aqueous solution of 0.5% weight/ volume of gentian violet+methylene blue (0.5% of each dye). The gloves were rinsed thoroughly (until the effluent was not obviously colored) and allowed to dry at room temperature. For the initial tests of the dye gloves, a treated glove was worn on one hand while an "undyed" control glove was worn on the other. After 3.5 hr the gloves were removed and each hand was pressed onto a contact plate to estimate the number of bacteria on the skin surface. No leaching of color from the dyed glove was apparent. After a 24 hr incubation the plate from the control hand was more than 50% covered by a diverse mixture of bacteria and fungi. The plate from the treated glove hand showed only scattered colonies with a coverage of less than 5%. This indicates that the treated gloves are quite effective in reducing the normal microbial load of the skin. If the skin surface had been precleaned (such as by sterile washing procedures), the treated gloves would provide an extra safety margin in preventing the spread of contaminants. Also, there have been reports in the medical literature that non-sterile latex gloves may harbor serious bacterial contamination. Pretreatment of gloves with disinfectant dyes would be expected to greatly reduce this problem.

However, the dyed gloves are most effective against limited contamination. In an experiment intended to model unusually heavy contamination a $1 \times 10^3$ bacterial/ml suspension of $E.\ coli$ was prepared and sprayed onto each hand. Sufficient solution was used to completely wet the hand. Then either a dyed or control glove was placed on the treated hands and was worn for 2 hr. The contact plate experiment was repeated as before. In this case significant growth of $E.\ coli$ was apparent with either the treated or the control glove. A colony count showed that the treated glove hand produced 136 colonies as compared to 194 colonies for the control plate. It would seem that while the treated glove is most effective under conditions of limited contamination, there is some effect even in the face of more massive contamination.

Dyed gloves from earlier experiments were reevaluated to estimate the operative like of the current invention. The gloves were dyed with the gentian violet/methylene blue mixture as already explained. In this case the gloves were stored in a dark drawer for approximately one year prior to testing. The gloves were tested against light contamination by spraying them with $1 \times 10^3$ bacterial/ml suspension of $E.\ coli$. The gloves were incubated for 5, 10, 20, or 20 min and then tested by being pressed to a contact plate of growth medium. None of the treatments showed bacterial growth indicating that a direct light spray of bacterial is completely killed by the gloves. This is in contrast to the earlier experiment where the hand rather than the glove was sprayed. In that case the gloves were less effective at killing bacteria probably because viable bacteria were protected by the topology of the skin surface from direct contact with the active glove surface. However, when the gloves were challenged by being directly touched to a heavily grown plate of bacteria, significant growth resulted. In this case it seems likely that the bacterial cells were piled, one atop another, on the glove surface so that many bacteria did not contact the active glove surface. In any case, dyed latex maintains its antibacterial properties for at least one year.

Vinyl gloves are commonly used for patient examinations and other laboratory uses. Vinyl gloves were died by immersion in the 0.5% dual dye solution. The gloves appeared to take up more than adequate color so they were removed from the dye solution and blotted dry. One dyed and one control glove was worn for two hours during routine laboratory tasks. The hands were then pressed onto contact plates which were incubated as above. In this case, the control hand showed 15 colonies whereas the treated hand showed 0 colonies. However, visible quantities of dye leached from the treated glove and visibly colored the hand. It would appear that the gloves should be dyed for a shorter period of time and/or rinsed more completely before use.

The vinyl glove experiment was repeated with the gloves being immersed for only 1.0 min after which the gloves were allowed to air dry for 24 hr. A single treated glove was worn for two hours a day for seven consecutive days. This was done to estimate the long-term activity of the disinfectant dye and to look for dye leaching. In no instance was any color observed to leach from the treated glove. The following table indicates colony growth (measured with contact plates) of the control (untreated glove) hand versus the treated glove hand.

| Day | Control (colony number) | Treated (colony number) |
| --- | --- | --- |
| 1 | 12 | 1 |
| 2 | 15 | 2 |
| 3 | 10 | 0 |
| 4 | 9 | 0 |
| 5 | 17 | 2 |
| 6 | 22 | 0 |
| 7 | 13 | 3 |

These results indicate that the treated vinyl gloves are highly effective against ordinary skin flora without visibly coloring the skin. Further there was no indication of any irritation or negative effect of the dyed gloves. This is not surprising since both methylene blue and gentian violet have a long history of topical use. They are generally non-irritating, and preliminary experiments indicate that dye treated polymer is also non-irritating. The unusual effectivness of the present material is probably due to the adsorption of the dye to the polymer which prevents it from washing away and becoming too dilute to be effective. The adsorbed dye presents a very high local concentration that effectively eliminates microbes. Presumably, the dye either inhabits adherence or transfers from the polymer to the microbial cells in contact with the treated polymer thereby killing them. It is fairly easy to test materials for suitability in the present invention. Effective materials will become readily colored by when treated with the microbicides. Furthermore, extensive washing will be unable to remove the tightly adsorbed antimicrobial dye.

Continued experimentation with various medical plastics has shown that blood clotting factors or other adherent proteins from body fluids appear to play an important role in infections and contamination of implanted polymeric surfaces. This is not entirely unexpected because it is known that formation of an adherent film of bacteria is an important step in the production of persistent infections. Bacteria rapidly form a polysaccharide or mucopolysaccharide film by which they adhere to various surfaces. Once such a film is formed, a persistent infection results. It is believed that an important effect of treating polymers with synthetic dyes or phenolic plant fractions is to inhibit the formation of such a bacterial film. An important aspect of "biocompatibility" of medically implanted materials is whether infective agents adhere to the materials. While most infective agents will not adhere to body tissue, such agents will adhere to many "non-native" materials—that is, to substances that are not native to the body. Thus, artificial heart valves, catheters and other implanted items may become coated with proteins that enhance or facilitate the formation of bacterial films. This property is often described in terms of being "antithrombogenic" because the natural blood clotting system appears to be involved with forming a proteinaceous coating on "nonnative" (foreign) materials. Platelets become activated by foreign surfaces and adhere thereto prompting the coagulation of one or more blood proteins. This thrombotic coating can then form the "toehold" for bacterial films.

It has now been discovered that the combination of meglumine (N-methylglucamine) with the organic dyes provides a significantly superior infection resistant surface. For the experiment a 1% weight/volume aqueous solution of meglumine was produced. Lengths of extremely fine nylon catheter material (outer diameter approximately 0.2 mm) were soaked in the meglumine for 24 hr and then air dried to provide a meglumine coated polymer. The coated catheters were then soaked in a 1% weight/volume aqueous solution of gentian violet plus methylene blue (i.e., 1% of each dye) for 24 hr. The treated catheters were then well rinsed in warm tap water and allowed to air dry for an additional 24 hr at room temperature.

A series of tests were then performed on the treated catheter material. Lengths of treated and untreated catheter were placed in 10 ml aliquots of fresh human plasma, and the plasma was clotted through the addition of 25 $\mu$M of $CaCl_2$. After the clot was formed the catheter lengths were carefully extracted and adherence of the clot was carefully examined. Lengths of the catheter material (both treated and untreated (control)) were placed in a suspension of $1 \times 10^4$ *Escherichia coli* cells in 50 ml of human plasma. Each day for 7 days sample catheters were removed from the plasma and plated on trypticase soy agar to asses the presence of adherent bacteria. In addition, catheters could be washed in running water for variable times (days) prior to the plasma/bacteria test.

It was observed that meglumine treated catheters were significantly darker than the untreated controls. Further, the treated catheters resisted adherence of the clots much more effectively than did the untreated catheters. Unwashed treated and control catheters resisted bacterial growth over the entire 7 day treatment. However, when catheters were prewashed, meglumine pretreatment allowed the treated catheters to resist bacterial growth. It is not clear whether this is due to the enhancement in initial dye binding due to the meglumine, whether the antithrombogenic properties of the meglumine prevent bacterial adherence or whether both (and possibly other factors) are at work. In any case it is clear that meglumine pretreatment enhances the gentian violet/methylene blue treatment. The meglumine also appears to work when applied simultaneously with the dyes; it is not clear if there is an advantage to simultaneous versus separate treatment. This may depend on dye concentrations and type of polymer being treated.

The current invention has been described as including the step of treating the formed polyrmer with a microbicide solution. This is currently the preferred method of making the treated polymer of the present invention although it is possible that the microbicide could be introduced during manufacture of the polymer, thereby simplifying the entire process.

Many alterations and modifications may be made by those having ordinary skill in the art without departing from the spirit and scope of the present invention. The definitions of the words or elements of the following claims are defined in this specification to include not only the combination of elements which are literally set forth, but all equivalent structure, material or acts for performing substantially the same function in substantially the same way to obtain substantially the same result.

I claim:

1. An antimicrobial organic polymeric material for medical and personal use comprising:

a solid organic polymer;

meglumine absorbed onto said organic polymer; and a disinfectant organic dye selected from the group consisting of methylene blue, acridine orange, gentian violet, brilliant green, acridine yellow, quinacrine, trypan blue, and trypan red absorbed onto said organic polymer.

2. The antimicrobial organic polymeric material of claim 1, wherein the organic polymer is selected from the group consisting of polyvinyl chloride, latex, polyurethane, polyacrylate, polyester, polyethylene terephthalate, polymethacrylate, nylon, silicone rubber, silicon elastomers, polystyrene, polycarbonate and polysulfones.

3. The antimicrobial organic polymeric material of claim 1, wherein the disinfectant organic dye comprises a mixture of an acidic and a basic dye.

4. The antimicrobial organic polymeric material of claim 1, wherein the disinfectant organic dye comprises a mixture of methylene blue and gentian violet.

5. A process for making an antimicrobial organic, polymeric material comprising the steps of:

absorbing meglumine to a solid organic polymer;

absorbing a disinfectant organic dye selected from the group consisting of methylene blue, acridine orange, gentian violet, brilliant green, acridine yellow, quinacrine, trypan blue, and trypan red to the organic polymer; and removing unabsorbed disinfectant organic dye from said polymer.

6. The process of claim 5, wherein the organic disinfectant dye comprises a mixture of an acidic and a basic dye selected from the group consisting of methylene blue, acridine orange, gentian violet, brilliant green, acridine yellow, quinacrine, trypan blue, and trypan red.

7. The process of claim 5, wherein the organic disinfectant dye comprises a mixture of methylene blue and gentian violet.

8. The process of claim 5, wherein the organic polymer is selected from the group consisting of polyvinyl chloride, latex, polyurethane, polyacrylate, polyester, polyethylene terephthalate, polymethacrylate, nylon, silicone rubber, silicon elastomers, polystyrene, polycarbonate and polysulfones.

9. An antimicrobial catheter comprising:

a catheter tip a length of tubing formed from an organic polymer communicating with said tip, wherein at least one of the tip and the tubing has absorbed to an exterior surface thereof meglumine and a mixture of methylene blue and gentian violet.

10. The catheter of claim 9, wherein the organic polymer is selected from the group consisting of polyvinyl chloride, latex, polyurethane, polyacrylate, polyester, polyethylene terephthalate, polymethacrylate, nylon, silicone rubber, silicon elastomers, polystyrene, polycarbonate and polysulfones.

* * * * *